United States Patent [19]

Hoffmann et al.

[11] 4,069,258
[45] Jan. 17, 1978

[54] CYCLOPENTENE DERIVATIVES

[75] Inventors: Werner Hoffmann, Neuhofen; Karl von Fraunberg, Bobenheim, both of Germany

[73] Assignee: BASF Aktiengesellschaft, Ludwigshafen, Germany

[21] Appl. No.: 666,630

[22] Filed: Mar. 15, 1976

[30] Foreign Application Priority Data

Mar. 29, 1975 Germany .............................. 2513996

[51] Int. Cl.$^2$ ...................... C07C 45/00; C07C 47/40
[52] U.S. Cl. .................................... 260/598; 252/522; 260/340.7; 260/340.9 R; 260/617 R; 560/220; 560/231; 560/238
[58] Field of Search ......................................... 260/598

[56] References Cited

U.S. PATENT DOCUMENTS 3,978,009  8/1976  Schulte-Elte .................... 260/598 X

FOREIGN PATENT DOCUMENTS 704,954  3/1965  Canada.

OTHER PUBLICATIONS

Houben–Weyl, Methoden der Organischen Chemie, Band VII, Teil I, Sauerstoffverbindungen II, 1954.

Primary Examiner—Ethel G. Love
Attorney, Agent, or Firm—Keil, Thompson & Shurtleff

[57] ABSTRACT

Cyclopentene derivatives (I)

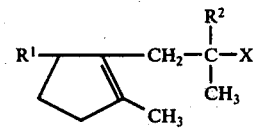

where $R^1$ is isopropyl or isopropenyl, $R^2$ is alkyl of 1 to 3 carbon atoms, X is —CHO, a dialkyl acetal or 1,2- or 1,3-alkylene acetal thereof where the acetal radical is of 2 to 6 carbon atoms, —CH$_2$OH or —CH$_2$OCOR$^3$ where $R^3$ is hydrogen or alkyl or alkenyl of up to 3 carbon atoms. The manufacture of I from the corresponding halomethyl cyclopentenes and aldehydes $R^2$—CH(CH$_3$)—CHO in the presence of a base and a quaternary ammonium salt, followed if desired by acetalization or conversion of the —CHO group to the —CH$_2$OH or —CH$_2$O—CO—R$^3$ groups. The compounds are useful as fragrance materials.

1 Claim, No Drawings

CYCLOPENTENE DERIVATIVES

The present invention relates to new cyclopentene derivatives of the general formula I

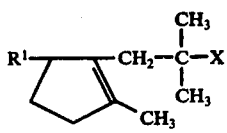

where $R^1$ is isopropyl or isopropenyl, $R^2$ is alkyl of 1 to 3 carbon atoms, X is CHO, a dialkyl-acetal or 1,2- or 1,3-alkylene-acetals thereof where the acetal radical is of 2 to 6 carbon atoms, $CH_2OH$ or $CH_2OCOR^3$ where $R^3$ is hydrogen or alkyl or alkenyl of up to 3 carbon atoms. The invention also relates to the manufacture of these compounds, and their use as fragrance materials and aromatics.

Cyclopentene derivatives of the general formula I in which X is CHO and $R^2$ is hydrogen, and their acetals, are disclosed in German Laid-Open Application No. 2,405,568, and may be used as fragrance materials. However, because they contain a reactive hydrogen atom in the α-position to the formyl group, these compounds are of limited stability. For example, if they are used as perfumes in alkaline media such as soaps and detergents, they undergo aldol condensations which detract from their fragrance characteristics. The light stability, which is important, inter alia, in perfumes and colognes, is also adversely affected by the presence of the mobile hydrogen.

The present invention seeks to enrich the art by providing new fragrance and aroma materials from the cyclopentene series.

We have found the new cyclopentene derivatives of the general formula I

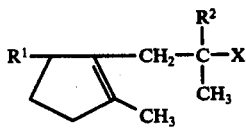

where $R^1$ is isopropyl or isopropenyl, $R^2$ is alkyl of 1 to 3 carbon atoms, X is CHO, $CH(OR^4)_2$,

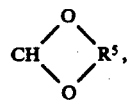

$CH_2OH$ or $CH_2OCOR^3$, $R^3$ is hydrogen or alkyl or alkenyl of up to 3 carbon atoms, $R^4$ is alkyl of 1 to 3 carbon atoms and $R^5$ is 1,2-alkylene or 1,3-alkylene of 2 to 6 carbon atoms, are valuable fragrance materials and aromatics, the acetals and aldehydes in particular being stable.

Further, we have found that the aldehydes of the general formula I are obtained when compounds of the general formula II

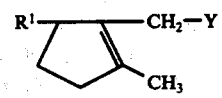

where Y is halogen, preferably chlorine or bromine, are reacted with aldehydes of the general formula III

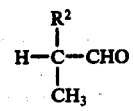

in the presence of bases and quaternary ammonium salts and that these may be acetalized e.g. by conventional methods to form the dialkyl acetals and 1,2- and 1,3-alkylene acetals of general formula I.

Further, we have found that the free aldehydes I may be reduced, e.g. by conventional methods, to the corresponding alcohols of formula I and that these may if desired be converted to the $R^3$—COOH esters.

The 1-methyl-2-halomethyl-3-isopropenylcyclopentenes, which are also new, may be obtained by halogenation of 1-methyl-2-methylene-3-isopropenylcyclopentan-1-ol, by, eg., reacting the latter by conventional methods with thionyl chloride, thionyl bromide, phosphorus trichloride, phosphorus tribromide or phosgene, expediently in an inert polar solvent, eg., dimethylformamide. The said cyclopentanol derivative is in turn obtainable in high yields by heating dehydrolinalool:

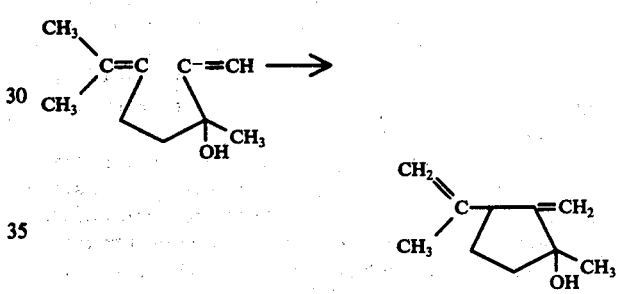

The most suitable starting compound III is isobutyraldehyde. To manufacture the compounds I, III is reacted, by conventional methods, in the presence of at least stoichiometric amounts of a strong mineral base such as sodium hydroxide or potassium hydroxide or, preferably, aqueous sodium hydroxide solution or potassium hydroxide solution and catalytic amounts of a quaternary ammonium salt. During the reaction, the quaternary ammonium salt is converted to the corresponding base which, being an organophilic substance, reacts more easily with II than does the mineral base. The reaction of III with the ammonium base in turn yields the hydrogen halide salt, from which the mineral base, in turn, liberates the ammonium base, and so on. Suitable quaternary ammonium salts are, eg., tetraethylammonium chloride, tetrabutylammonium bromide and tetrabutylammonium iodide. They are used in amounts of from about 0.001 to 0.1, preferably from 0.01 to 0.05, mole per mole of II; larger quantities are not essential, but do not interfere either. The aldehydes I can be acetalized in the conventional manner, in the presence of catalytic amounts of an acid. Examples of preferred alcohol components are methanol, ethanol, ethylene glycol, 1,2-propylene glycol or 1,3-butylene glycol.

The following are examples of products which can be isolated from the reaction mixture by distillation and can be subjected to further purification in the same manner: 1-methyl-2-(2,2-dimethyl-2-formylethyl)-3-isopropenylcyclopent-1-ene, 1methyl-2-(2-methyl-2-ethyl-2-formylethyl)-3- isopropenylcyclopent-1-ene, 1-methyl-2-(2-methyl-2-isopropyl-2-formylethyl)-3-isopropenylcyclopent-1-ene, 1-methyl-2-(2-methyl-2-propyl-2-formylethyl)-3-isopropenylcyclopent-1-ene and the acetals of these aldehydes.

The free aldehydes I — which themselves have valuable fragrance characteristics — may be used for the manufacture of further fragrance materials by converting them, in the conventional manner, with reducing agents such as sodium boranate, to the alcohols I$a$

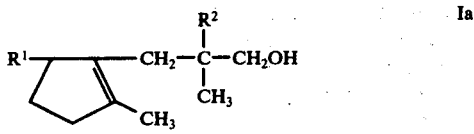

and further converting these to their esters with carboxylic acids R$^3$—COOH. Another very suitable method for the preparation of the alcohols I$a$ is reduction with aluminum triisopropylate by the Meerwein-Ponndorf method.

In general, compounds I which are preferred both in respect of their properties as end products, and as intermediates, are those where R$^1$ is isopropenyl, since the compounds derived therefrom have a fresher note than the isopropyl derivatives. The isopropyl derivatives can be prepared from the corresponding isopropenyl compounds by conventional partial hydrogenation.

With increasing size of the alkyl groups R$^2$ and R$^3$, the fragrance becomes suggestive of musk. Parallel thereto, its tenacity increases.

The perfumes according to the invention, the inexpensive availability of which is an important advantage, are generally suitable as ingredients in cosmetics of all kinds and in soaps and detergents, the concentrations used being from 0.1 to 5 percent by weight. They may also be used for flavoring foodstuffs and beverages. In view of their chemical stability, they are of particular importance in compositions which are exposed to light or — as in the case of detergents — are exposed to alkaline reagents.

EXAMPLE 1

1-Methyl-2-(2,2-dimethyl-2-formylethyl)-3-isopropenylcyclopent-1-ene

A mixture of 857 g (5 moles) of 1-methyl-2-chloromethyl-3-isopropenylcyclopentene and 360 g (5 moles) of isobutyraldehyde was added in the course of 5 hours, whilst stirring, to a mixture of 480 g of 50% strength sodium hydroxide solution, 24 g of tetrabutylammonium iodide and 500 ml of toluene, at 80° C. The organic phase was then separated off and washed repeatedly with 200 ml portions of water, the toluene was stripped off and the residue was distilled in a rotary evaporator; boiling point 75°-77° C/0.3 mm Hg; n$_D^{25}$: 1.4788; the structure was confirmed by the nuclear resonance spectrum; yield: 76%.

The compound has a floral fragrance suggestive of sandalwood.

The starting compound was manufactured by chlorinating 760 g (5 moles) of 1-methyl-2-methylene-3-isopropenylcyclopentanol with phosgene in a mixture of 440 g of dimethylformamide and 1.5 l of toluene in the course of 7 hours at from 0° to 5° C. After washing the organic phase with sodium carbonate solution and water, the chloromethylcyclopentene was obtained in 89% yield by distillation. Boiling point: 45° C/4 mm Hg;

n$_D^{25}$: 1.4928; the structure was confirmed by the nuclear resonance spectrum.

EXAMPLE 2

1-Methyl-2-(2-methyl-2-propyl-2-formylethyl)-3-isopropenylcyclopent-1-ene

By following the procedure described in Example 1, but with 2-methylvaleraldehyde (R$^2$ = propyl) instead of isobutyraldehyde, 1-methyl-2-(2-methyl-2-propyl-2-formylethyl)-3-isopropenylcyclopentene was prepared in 85% yield. Boiling point: 68°-70° C/0.1 mm Hg; n$_D^{25}$: 1.4808; the structure was confirmed by the nuclear resonance spectrum.

The compound has a floral, woody fragrance of good tenacity.

EXAMPLE 3

1-Methyl-2-(2,2-dimethyl-3-hydroxypropyl)-3-isopropenylcyclopent-1-ene

A solution of 1 l of ethanol and 27 g (0.7 mole) of sodium boranate was added in the course of 2 hours to 412 g (2 moles) of the product from Example 1, at from 25° to 30° C. The ethanol was then stripped off and the residue was acidified with dilute sulfuric acid, washed and then worked up by distillation in the conventional manner. Boiling point: 77° C/0.1 mm Hg; n$_D^{25}$: 1.4894; yield 82%; the structure was confirmed by the nuclear resonance spectrum.

The compound has a typical sandalwood odor.

EXAMPLE 4

1-Methyl-2-(2,2-dimethyl-3-acetoxypropyl)-3-isopropenylcyclopent-1-ene

This compound was prepared by esterifying 32 g (0.25 mole) of the product from Example 3 with 24 g (0.3 mole) of acetyl chloride and 24 g (0.3 mole) of pyridine at from 15° to 20° C. On working up in the conventional manner, the ester was obtained in 95% yield; boiling point: 88°-90° C/25 mm Hg; n$_D^{25}$: 1.4743; the structure was confirmed by the nuclear resonance spectrum. Fragrance: musk-like, floral; good tenacity.

EXAMPLE 5

1-Methyl-(2,2-dimethyl-2-formylethyl)-3-isopropenylcyclopent-1-ene-1,2-ethylene-acetal 41 g (0.2 mole) of the product from Example 1 in 100 ml of methylene chloride were acetalized with 0.5 g of p-toluene-sulfonic acid and 25 g of ethylene glycol. On working up in the conventional manner, the acetal was obtained in 82% yield; boiling point: 80°-85° C/0.3 mm Hg; n$_D^{25}$: 1.4900; the odor resembles that of the free aldehyde, but is somewhat fresher.

EXAMPLE 6

1-Methyl-2-(2,2-dimethyl-3-hydroxypropyl)-3-isopropenylcyclopent-1-ene 103 g (0.5 mole) of the product from Example 1 were reduced with 60 g of isopropanol and 20 g of aluminum triisopropylate by the Meerwein-Ponndorf method. The conversion was 78% and the yield of the above compound (for characteristics thereof, see Example 3), based on the above conversion, was 73%.

EXAMPLE 7

1-Methyl-2-(2,2-dimethyl-3-acetoxypropyl)-3-isopropylcyclopent-1-ene 10 g of the product from Example 4 in solution in ethanol were partially hydrogenated at 50° C under a hydrogen pressure of 100 bars, in the presence of 1 g of Raney nickel, to give the above compound. Yield 85%, boiling point 70°–76° C/0.05 mm Hg, $n_D^{25}$: 1.4622. Somewhat blander odor than the analogous isopropenyl compound (see Example 4).

EXAMPLE 8

1-Methyl-2-(2-methyl-2-propyl-3-hydroxypropyl)-3-isopropenyl-cyclopent-1-ene

This compound was prepared from the product from Example 2 by reduction with sodium boranate, as described in Example 3. Yield 55%; boiling point 110°–114° C/0.5 mm Hg; $n_d^{25}$: 1.4910. Odor: mold, green and herbaceous.

EXAMPLE 9

1-Methyl-2-(2-methyl-2-propyl-3-acetoxypropyl)-3-isopropenylcyclopent-1-ene

Esterification of the product from Example 8 with acetyl chloride by the method of Example 4 gave the above compound in 86% yield. Boiling point 70°–75° C/0.05 mm Hg, $n_D^{25}$: 1.4780. Odor: faint, woody, persistent tenacity.

EXAMPLE 10

1-methyl-2-(2,2-dimethyl-2-formylethyl)-3-isopropenyl-cyclopent-1-ene-1,3-butylene-acetal This compound was obtained in 64% yield by acetalizing the product from Example 1 with a molar excess of butane-1,3-diol in the presence of p-toluenesulfonic acid, in benzene solution. Boiling point 85°–90° C/0.1 mm Hg; $n_D^{25}$: 1.4840; odor: green and woody, floral.

EXAMPLE 11

1-Methyl-2-(2,2-dimethyl-2-formylethyl)-3-isopropenylcyclopent-1-ene-dimethylacetal On acetalizing the product from Example 1 with an excess of methanol and equimolar amounts of methyl orthoformate in the presence of p-toluenesulfonic acid, the above compound was obtained in 82% yield; boiling point 81°–83° C/0.3 mm Hg; $n_D^{25}$: 1.4750; odor: resembling balsam, woody, with a green note.

EXAMPLE 12

1-Methyl-2-(2,2-dimethyl-3-formyloxypropyl)-3-isopropenylcyclopent-1-ene 40 g of the product from Example 3 were stirred with 200 g of formic acid in the presence of 10 g of a molecular sieve (3 Angstrom) as an esterifcation catalyst, for several hours at room temperature. On working up in the conventional manner, the above formic acid ester was obtained in 77% yield. Boiling point 63°–65° C/0.1 mm Hg; $n_D^{25}$: 1.4784; odor: musk-like, sweet, woody.

We claim:

1. A process for the manufacture of a cyclopentene derivative of the formula I

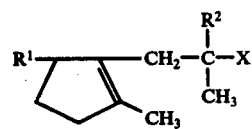

where $R^1$ is isopropyl or isopropenyl, $R^2$ is alkyl of 1 to 3 carbon atoms, X is CHO which comprises: reacting a compound of the formula II

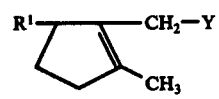

where Y is halogen with an aldehyde of the formula III

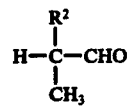

in the presence of an aqueous solution of a strong base and in the presence of a catalytic amount of a quaternary ammonium salt.

* * * * *